United States Patent
Koehler et al.

(10) Patent No.: US 10,339,674 B2
(45) Date of Patent: Jul. 2, 2019

(54) QUANTITATIVE DARK-FIELD IMAGING IN TOMOGRAPHY

(71) Applicant: KONINKLIJKE PHILIPS N.V., Eindhoven (NL)

(72) Inventors: Thomas Koehler, Norderstedt (DE); Bernhard Johannes Brendel, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 62 days.

(21) Appl. No.: 15/328,645

(22) PCT Filed: Aug. 4, 2015

(86) PCT No.: PCT/EP2015/067864
§ 371 (c)(1),
(2) Date: Jan. 24, 2017

(87) PCT Pub. No.: WO2016/023782
PCT Pub. Date: Feb. 18, 2016

(65) Prior Publication Data
US 2017/0213365 A1    Jul. 27, 2017

(30) Foreign Application Priority Data
Aug. 13, 2014    (EP) .................................... 14180751

(51) Int. Cl.
*G06K 9/00*    (2006.01)
*G06T 11/00*    (2006.01)
(Continued)

(52) U.S. Cl.
CPC ............ *G06T 11/003* (2013.01); *A61B 6/484* (2013.01); *A61B 6/5258* (2013.01); *G01N 23/04* (2013.01);
(Continued)

(58) Field of Classification Search
None
See application file for complete search history.

(56) References Cited

U.S. PATENT DOCUMENTS 8,121,249 B2    2/2012  Wang
2005/0251354 A1*  11/2005  Guo ................... G06F 17/5036
                                                            702/79

(Continued)

FOREIGN PATENT DOCUMENTS

| WO | 2013171657 | 11/2013 |
| WO | 2014002026 | 1/2014 |
| WO | 2014/103269 | 7/2014 |

OTHER PUBLICATIONS

Yang, et al., "The second-order differential phase contrast and its retrieval for imaging with x-ray Talbot interferometry", Medical Physics, vol. 39, No. 12, Nov. 26, 2012.
Koehler, et al., "Non-scatter contributions to the dark-field signal in differential phase contrast imaging", AIP Conference Proceedings, vol. 1466, Jul. 31, 2012.
Pfeiffer et al in "Phase retrieval and differential phase-contrast imaging with low-brilliance X-ray sources," Nature Phys. Lett. 2, 258-261 (2006).

(Continued)

Primary Examiner — Kevin Ky
(74) Attorney, Agent, or Firm — Larry Liberchuk (57) ABSTRACT

A signal processing apparatus and a related method. In particular, the apparatus includes a novel image reconstructor to reconstruct cross sectional images of a specimen from interferometric projection data (m). The reconstructor (RECON) is based on a new forward model that accounts for cross-talk of a phase contrast signal into a dark field signal.

13 Claims, 5 Drawing Sheets (51) Int. Cl.
*A61B 6/00* (2006.01)
*G01N 23/04* (2018.01)
*G01N 23/046* (2018.01)

(52) U.S. Cl.
CPC ..... *G01N 23/046* (2013.01); *G01N 2223/401* (2013.01)

(56) References Cited

U.S. PATENT DOCUMENTS

| | | |
|---|---|---|
| 2011/0293064 A1 | 12/2011 | Huang |
| 2014/0010344 A1 | 1/2014 | Nagatsuka |
| 2014/0169522 A1 | 6/2014 | Hoshino |
| 2015/0124927 A1 | 5/2015 | Koehler |
| 2015/0187096 A1* | 7/2015 | Baturin ............ G01T 1/164 382/132 |

OTHER PUBLICATIONS

M Bech at el, "Quantitative X-ray dark-field computed tomography", Phys. Med. Biol. 55 (2010) 5529-5539.

Koehler et al, "Iterative reconstruction for differential phase contrast imaging", pp. 4542-4545, Med. Phys. 38 (8), Aug. 2011.

Ritter et al in "Simultaneous maximum-likelihood reconstruction for x-ray grating based phase-contrast tomography avoiding intermediate phase retrieval", Phys. Med, 2013.

Yashiro, et al., "On the origin of visibility contrast in x-ray Talbot interferometry", Opt Express 18, 16890-16901 (2010).

Cong, et al., "Dark-field Tomography: Modeling and Reconstruction" 2010.

Pfeiffier, et al., "Hard-X-Ray dark-field imaging using a grating interferometer", Nature Materials, vol. 7, Feb. 2008.

* cited by examiner

QUANTITATIVE DARK-FIELD IMAGING IN TOMOGRAPHY

CROSS REFERENCE TO RELATED APPLICATIONS

This application is the U.S. National Phase application under 35 U.S.C. § 371 of International Application No. PCT/EP2015/067864, filed Aug. 4, 2015, published as WO 2016/023782 on Feb. 18, 2016, which claims the benefit of European Patent Application Number 14180751.1 filed Aug. 13, 2014. These applications are hereby incorporated by reference herein.

FIELD OF THE INVENTION

The invention relates to image signal processing apparatus, to an image signal processing method, to a computer program product and to a computer readable medium.

BACKGROUND OF THE INVENTION

Differential phase contrast imaging is an imaging technique that uses an interferometer comprised of gratings to image the phase change induced by the object one wishes to image. When processing phase contrast image data there is another signal emerging that recently caught the attention of the research community. This is the dark field signal that relates to loss of coherence suffered by an electro-magnetic wave in its passage through the imaged object. It has been observed however that dark field images (as tomographically reconstructable from such dark field signals) are sometimes inflicted by artifacts.

SUMMARY OF THE INVENTION

There may therefore be a need for a method and related system to improve the fidelity or accuracy of dark field images.

The object of the present invention is solved by the subject matter of the independent claims with further embodiments incorporated in the dependent claims.

It should be noted that the following described aspect of the invention equally apply to the image signal processing method, to the computer program element and to the computer readable medium.

According to a first aspect of the invention, there is provided an image signal processing apparatus, comprising:

input port for receiving interferometric measurement data detected at a detector in response to an X-ray beam incident on said detector after projection of said beam through a specimen to be imaged, the data comprising a phase contrast signal and a dark field signal;

a reconstructor configured to execute an image reconstruction algorithm to reconstruct at least the dark field signal into a dark field image, $\varepsilon$, wherein the reconstruction algorithm is based on a forward model that incorporates a model component configured to capture cross-talk of the phase contrast signal into the dark field signal;

output port for outputting at least the reconstructed dark field image $\varepsilon$.

In particular, the phase contrast signal may be a differential phase contrast signal. The signals are obtained by allowing an X-ray beam to path through the specimen and at least two gratings of an interferometric arrangement.

Because the proposed method specifically accounts for the cross-talk between the image signals, in particular by using a specific (or, in one embodiment explicit) cross-talk component, the derived dark-field imagery suffers from fewer (or no) artifacts.

According to one embodiment, the forward model is a composite forward model formed from a combination of i) a dedicated forward model for the differential phase contrast signal and ii) a dedicated forward model for the dark field signal. The forming of the combination may involve non-linear operations but may involve only linear operations in alternative embodiments. According to one embodiment, the cross-talk model component is proportional to an absolute value of a partial spatial derivative of the or a dedicated forward model for the differential phase contrast signal.

According to an alternative embodiment, rather than having a composite forward model made up from dedicated forward models for each of the two signals, the forward model is a common one for both, the phase contrast signal and the dark field signal.

Having the option for common or composite forward models affords increased flexibility in processing the measurement data (sinogram). The sinogram can either be pre-analyzed (by suitably signal processing) into respective sinograms for the two channels (phase contrast and dark-field, respectively) and then processed as per one embodiment of the proposed method or the sinogram can be processed directly by using the common forward model as alternatively proposed herein.

According to one embodiment, the common forward model includes a model component for the phase contrast signal and model component for the dark field signal, wherein the cross-talk model component is proportional to an absolute value of a partial spatial derivative of the model component for the phase contrast signal. According to one embodiment, the reconstruction algorithm is iterative. According to one embodiment, the iterative reconstruction algorithm is driven by an optimization of an objective function.

According to one embodiment, the objective function incorporates a residue in respective of the forward model.

In one embodiment, the objective function is a common one for both signals and the two signals are solved for together. The contributions of both channels to the objective function are therefore accounted for which in turn has been observed to yield imagery of high fidelity.

According to one embodiment, a geometry of the beam is parallel or divergent, for instance cone-beam. If the geometry is a divergent one, the forward model may include a correction component.

The dark field signal is a superposition of scattering and contributions from refraction. The proposed system operates to estimate the non-scatter contribution to the dark-field signal during reconstruction and thus provides a reconstructed dark-field image that largely, if not solely, corresponds to a reconstruction of actual material scattering properties.

Previous reconstruction algorithms for the dark field signal, either FBP based or iterative, lead to severe artifacts. One of the reasons for the presence of artifact in FBP methods is that the refraction contribution (that is, the cross-talk) to the dark-field signal does not as such comply with a conventional model assumption of a "line integral". The proposed iterative reconstruction with the cross-talk modelling provides a way around this non-compliance with the line integral paradigm.

DETAILED DESCRIPTION OF EMBODIMENTS

Figure 1:
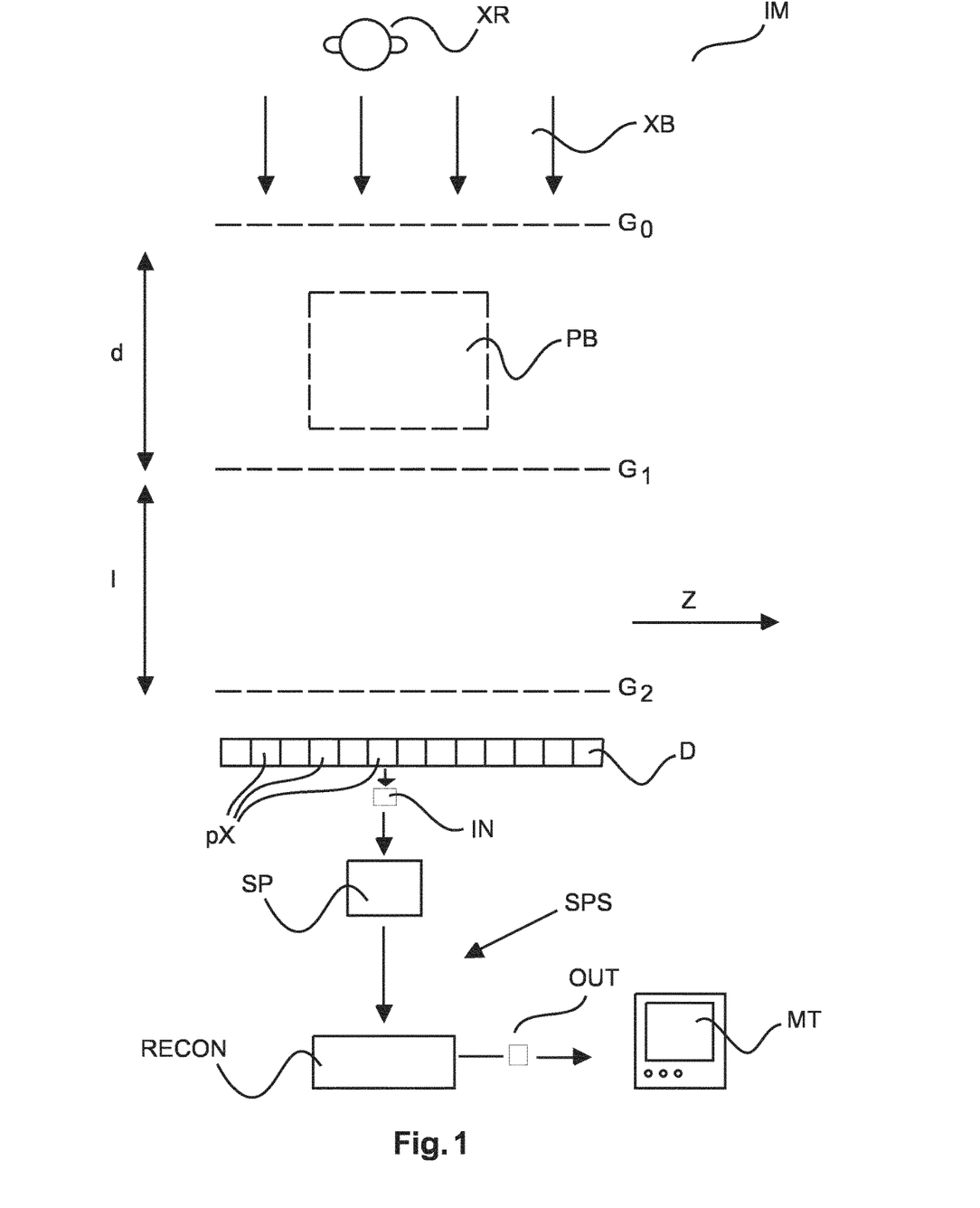
FIG. 1 shows an x-ray imaging system including interferometric gratings.

With reference to FIG. 1 there are shown components of an x-ray imaging system (IM) including interferometric equipment. The imaging system may be a computed tomography scanner (CT) or another X-ray imaging modality (eg, of the rotational C/U-arm type or other).

Broadly, x-ray radiation emitted from an x-ray source XR passes through an examination region and is then incident on a detector D.

In the examination region there resides an object PB to be imaged. The x-ray beam when looked at it wave optically, defines an electromagnetic wave that propagates through the examination region and interacts with matter in the specimen PB to be imaged.

In CT, at least the x-ray source XR is mounted on a rotatable gantry to project x-ray waves through the specimen PB along a plurality of projection directions.

The interaction of the wave with the matter results in the wave being modified. The modification includes on the one hand attenuation which is what is usually studied in traditional x-ray imaging. Attenuation is the result of the wave being absorbed and Compton scattered. Another modification relates to a phase change of the wave as it passes through the matter. This wave change can be understood by a change of direction of the wave front. Finally, and of primary interest herein, the wave is also subjected to another type of scattering, commonly called small angle scattering. It is type of scattering that one wishes to image in dark-field imaging where the contrast corresponds to the amount of local small angle scattering. Small angle scattering is assumed to be caused by interaction of the wave with micro-structures in the specimen PB. Small angel scattering can be understood as a loss of coherence when the wave passes first through the interferometric equipment and then through the matter. Wave optically, loss of coherence can be understood as a disturbance imparted by the matter on the wave in form of bending or warping the wave front. Whereas traditional absorption based x-ray imaging studies the distribution of the linear attenuation co-efficient in the specimen, in phase contrasting imaging one studies the distribution of the refractive index in the specimen. In dark-field imaging one asks how individual volume points in the specimen PB contribute to the loss of coherence suffered by the wave. This contribution is measured by a quantity called visibility V. More particularly, dark field imaging relates to the loss of visibility of fringes created by a phase grating $G_1$.

In CT one thinks of the examination region as a portion in space divided up into volume elements or "voxels". Because the specimen resides in the examination region this grid of voxels imparts a voxelization of the specimen PB itself. In computed tomography one looks at two different spaces: on the one hand the "image space" made up of the voxels and on the other hand the "projection space" which is made up of the projection data registered at the detector. In computed tomography one wishes to reconstruct, that is, compute values for the voxels in image space from the projection data in projection space. This is understood as an inverse problem. More particularly, and of chief interest herein, reconstruction of a dark field image is essentially the task of computing the relevant quantity of interest, in this case visibility V, per voxel for the dark field image, from the projection data. The collection of reconstructed voxels represents one or more cross sectional images (referred to herein as the dark field image) in respective planes through the specimen for the dark field signal.

It has been found that if one detects the x-ray wave at the detector after interaction of the wave with both, the interferometric equipment and the specimen PB, then any of the three signals of interest, namely the attenuation, the phase and the dark field signal are all recoverable from the detector signal(s) caused by the impinging wave.

The interferometric equipment is essentially a system of gratings. An exemplary interferometric set up will now be explained briefly with further reference to FIG. 1. The interferometric equipment ("interferometer") as explained herein is purely an exemplary embodiment and other arrangements are also envisaged.

The interferometer (which in one non-limiting embodiment is of the Talbot type or of the Talbot-Lau type) includes two $G_1$, $G_2$ (Talbot type) or more, preferably, three gratings $G_0$, $G_1$ and $G_2$ (Talbot-Lau type). The first attenuation grating ("source grating") $G_0$ at the X-ray source side has a period $p_0$ to match and cause spatial coherence of the X-ray radiation wave front emitted at the X-ray source XR.

A phase grating $G_1$ (having period $p_1$) is placed at distance d from the X-ray source and causes an interference pattern with period $p_2$ further downstream. Said interference pattern can be detected by detector D. Now, when a specimen PB (to be imaged) is introduced in the examination region between the X-ray source and the detector, the phase of the interference pattern is then shifted.

Unfortunately the phase shift of the interference pattern is typically too small to be directly spatially resolved. The resolution powers of most X-ray detectors would not allow this. Therefore in order to "sample" this interference pattern phase shift, a second, attenuation grating $G_2$ with the same period $p_2$ as the interference pattern is placed at a distance l from grating $G_1$.

The phase shift sampling can be achieved in a plurality of different ways all of which are envisaged herein.

For instance, in one embodiment a relative motion is effected between the detector D and at least one of the gratings. This can be achieved in one embodiment by "phase stepping" where an actuator is used to laterally move for instance, analyzer grating $G_2$ across different, discrete grating positions and then measure at each grating position the intensity at each pixel px. "Lateral" motion means herein along z direction (see FIG. 1), that is, motion in a direction perpendicular to the propagation direction of the wave XB and the "trench" directions of the gratings. The phase-stepping approach has been described by F. Pfeiffer et al in "Phase retrieval and differential phase-contrast imaging with low-brilliance X-ray sources," Nature Phys. Lett. 2, 258-261 (2006). For accurate results the distances d, l ("Talbot distances") between the gratings must be carefully adjusted as explained in the Pfeiffer reference.

In other embodiments, some of the other gratings ($G_0$ or $G_1$) are moved relative to G2 and/or it is the specimen itself that is moved. Other options include effecting a focal point shift in the X-ray source.

No matter the sampling method used, the upshot is that in general, the intensity I at each pixel will be found to oscillate to form a local intensity curve for that detector-pixel path. In other words, each pixel records a time series of different intensities (at the respective pixel) as a function of time (or better as a function of the different grating positions) during motion of the analyzer grating G2. As mentioned earlier, it is this oscillating intensity signal I at each pixel px that "encodes" amongst other quantities the phase shift (or refraction) and the dark-field signal (or visibility).

If the x-ray imaging system is of the CT scanner type, the intensity signals for each pixel will be recorded from different projection directions.

The collection of intensities as recoded per pixels (and in CT, per projection direction) will be referred to herein as interferometric projection raw data or the "common" sinogram m.

The common sinogram is forwarded from the detector output electronics to a signal processing chain SPS that includes a reconstructor module RECON.

The reconstructor module RECON operates to reconstruct the intensity signals from the plurality of directions into a cross sectional image of the specimen.

In one embodiment, but not necessarily in all embodiments, the signal processing chain includes an analyzer module SP interposed between detector D and reconstructor RECON. The analyzer module SP, eg a Fourier analyzer (preferably arranged as a fast Fourier transformer FFT), operates to decompose the common sinogram m into two or three separate sinograms, one for each of the image signal channels or interest. In particular the analyzer module SP splits up the common sinogram into a phase contrast sinogram $m_\delta$ and the dark field sinogram $m_\epsilon$. This analysis of the oscillating intensities per pixel into the two or three signals/ sinograms (the attenuation signal being the third component) has been described more fully elsewhere, for instance on p 5531, eqs (1), (4) in M Bech at el, "Quantitative X-ray dark-field computed tomography", Phys. Med. Biol. 55 (2010) 5529-5539, incorporated herein by reference in its entirety. Briefly, the sinograms for the phase signal and dark-field signal (the visibility that is) can be computed from the zeroth and first-order component of the respective intensity I oscillation as detected by respective detector pixels. In other words the Fourier analyzer SP operates per pixel and projection direction on the respective intensity signals in the common sinogram to achieve the decomposition into the two dedicated sinograms $m_\delta$ and $m_\epsilon$ Therefore, depending on the embodiment, the reconstructor RECON receives either the common sinogram and reconstructs in particular the dark field image therefrom or, in another embodiment, the reconstructor receives at least the two sinograms $m_\delta$ and $m_\epsilon$ and uses, as proposed herein in one embodiment, both to reconstruct in particular the dark field image. Suitable visualization/rendering modules can then operate to visualize the respective cross-sectional reconstructions on a monitor or display MT.

It is proposed herein to use an iterative reconstruction scheme and the proposed method includes a new objective function which is used to drive the iteration. In particular, an optimization procedure of said objective function yields an update function with which an initial guess for the reconstructed image can be iteratively updated to so arrive at the respective images. It should be understood that although the main focus here is on the dark field image, the reconstruction always includes estimation of at least one (in many cases both) of the other two signals as well, in particular the phase contrast image. In fact, according to one embodiment, there is proposed a common objective function that consolidates the information from two of those channels, namely from the phase contrast channel and the dark field image channel.

One key point in our approach is to estimate the non-scatter contribution to the dark-field signal during reconstruction and thus to provide a reconstructed scatter image that is solely or at least largely, if note solely, a reconstruction of material scattering properties in the specimen PB. It has been observed that the accuracy and fidelity of the reconstructed data according to the proposed method is superior to previous reconstructions of the dark field image signal. Those reconstructions were frequently found to be riddled with artifacts.

Figure 2:
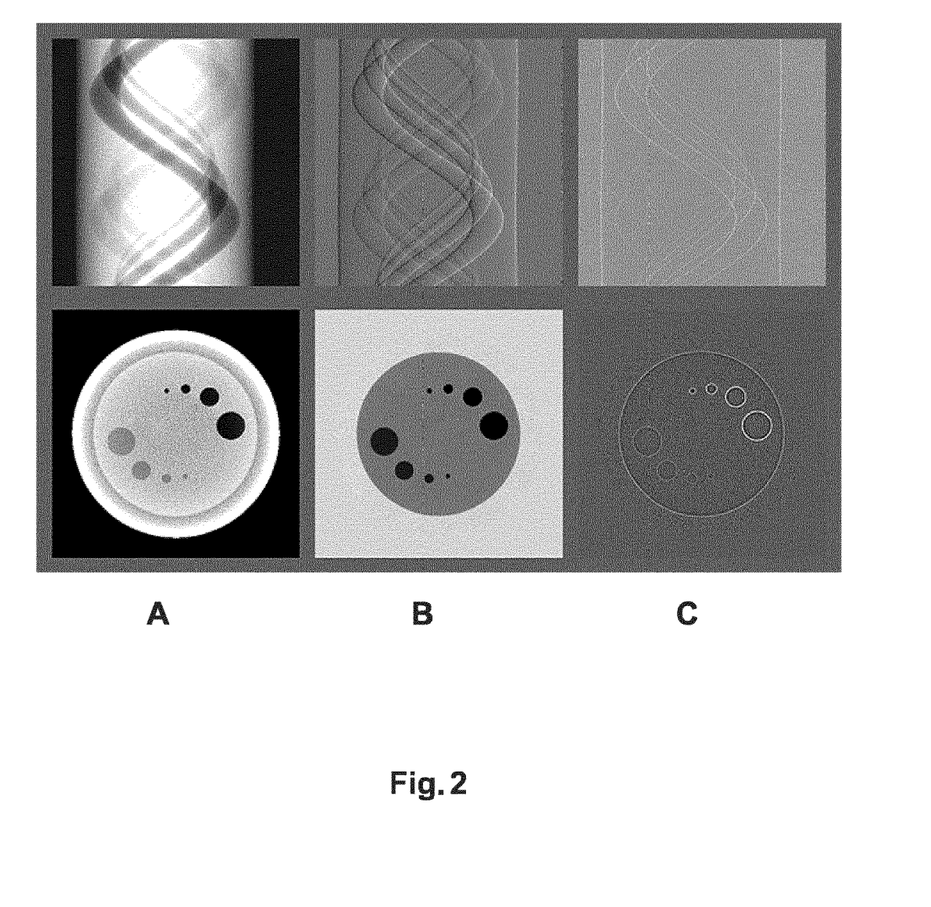
FIG. 2 shows reconstructed attenuation, phase and dark field images and their respective projection data as detected by a detector of the imaging system in FIG. 1.
Figure 3:
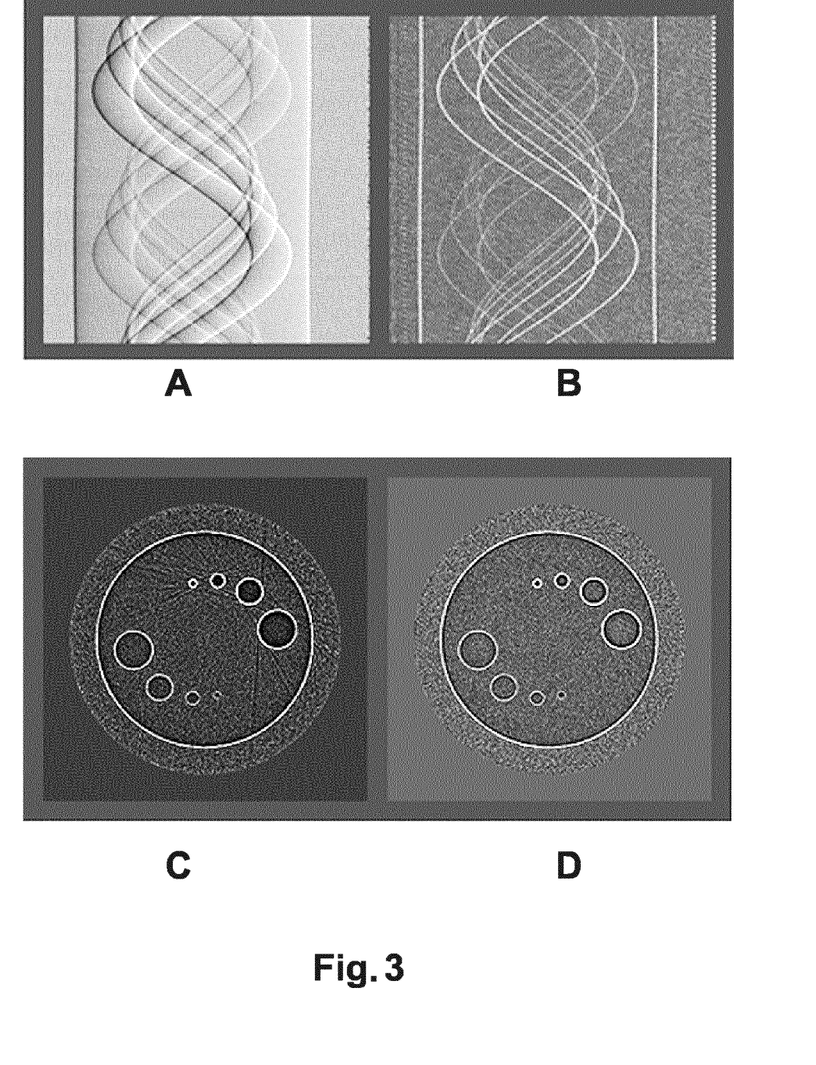
FIG. 3 shows in the upper row a differential phase sinogram and an image of the absolute values of the derivative of the differential phase sinogram, with the lower row showing the respective reconstructed images.
Figure 4:
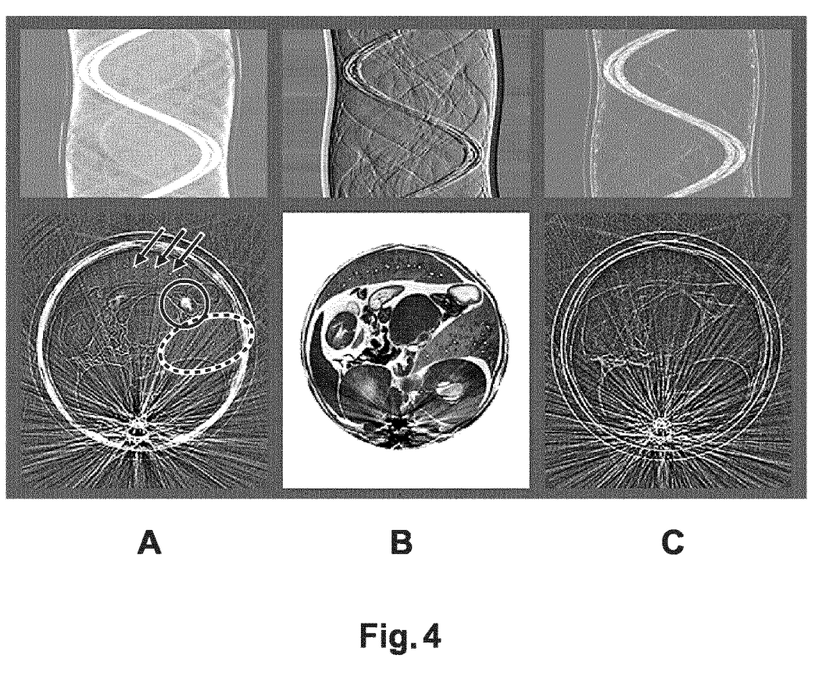
FIG. 4 shows, in the top row, a dark field sinogram, a differential phase sinogram and the absolute values of the derivative of the differential phase sinogram, with the lower row showing the respective reconstructed images.

Before providing further details on the proposed reconstructor, reference is now made to the following FIGS. 2-4 where we examine certain visual properties of dark field imagery and their sinograms phase to better motivate the proposed algorithm.

It has also been reported that a rapid change in the x-ray wave-front as caused for instance by edges in the object can cause a dark field signal response. In other word there is a certain cross-talk from the phase contrast signal into the dark field signal.

FIG. 2 shows for a phantom scan the three signals, namely attenuation in column A, phase (i.e. refractive index) in column B, and dark-field signal in column C. The top row shows the sinograms, bottom the reconstructed images. Apparently, the dark-field signal does not form a consistent sinogram (as only the traces of the edges of the object are visible), resulting in a pure edge image, that does not represent the local scattering properties of any object, since negative scattering would amount to an increase in coherence.

FIGS. 3 and 4 show a few image experiments to illustrate that an "edge contribution" to the scatter signal can in fact be estimated from the differential phase contrast signal.

More particularly, upper row in FIG. 3 shows again the differential phase contrast sinogram A) (the same as in FIG. 2) and the absolute value of its derivative B). As can be seen from the Figs., the edge sinogram look qualitatively very similar to the dark field sinogram (column C), top right in FIG. 2) and a filtered-back projection (FBP) of this edge sinogram looks almost exactly like the reconstructed scatter image, see C and D in the bottom row of FIG. 3.

A more detailed, real life example is given in FIG. 4, where image data from a mouse scan are shown. The upper panes in columns A, B, C are, respectively, the dark field sinogram, the differential phase sinogram, and "edges" derived from the differential phase sinogram (B) by differentiation. The bottom row across the respective columns A-C shows the respective tomographic reconstruction (obtained by FBP). A visual comparison of the dark field image with the reconstructed phase image again confirms that a lot of image features coincide with edges in the phase contrast image. In fact many features of the dark field image can also be well reproduced by the edge-image derived from the differential phase contrast sinogram by taking the absolute value of its derivative followed by an FBP reconstruction. However, there are certain features in the dark field image (indicated by arrows, the dashed ellipse and the circle in lower pane of column A in FIG. 4, bottom left) which are not visible in the edge image, and can thus be attributed to local scattering properties of the mouse.

The artifacts previously reported in reconstructed dark field imagery have been found to relate at least partly to the amount of cross-talk as such does not lend itself to the usual line integral model which one normally assumes when doing tomographic reconstruction. The line integral model supposes that the detected projection data corresponds to an accumulation of the quantity of interest along a certain path that is the path of the line integration. Although the line integral model assumption is a valid one for attenuation signal and the phase contrast signal, the situation is different for the phase signal induced cross-talk in the dark field signal as this cross-talk cannot be said to accumulate along the considered projection path. However, via the proposed iterative reconstruction method a formulation has been found where the dark field image signal can be suitably expressed as the line integral assumption for the dark-field signal is no longer required.

Figure 5:
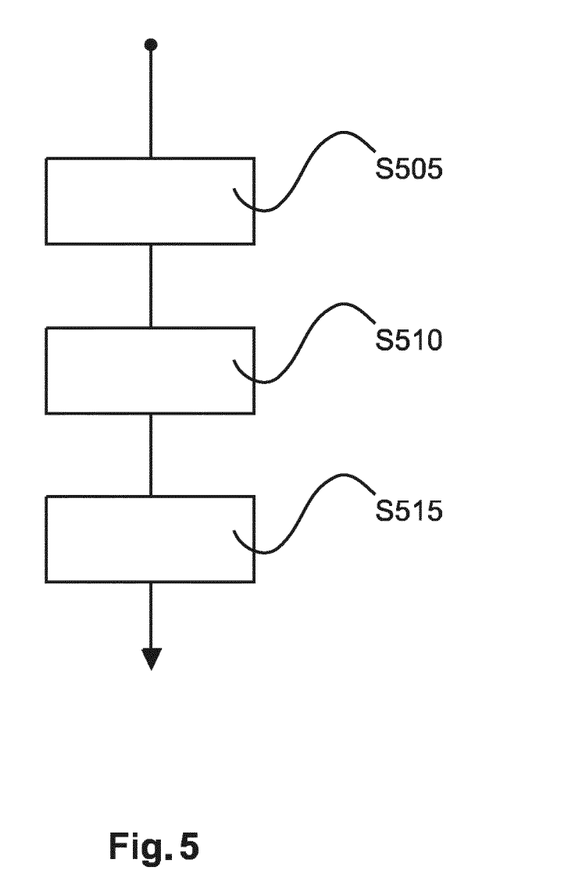
FIG. 5 shows a flow chart of an image signal processing method.

With reference to FIG. 5 the operation of reconstructor RECON is now explained in more detail.

In a preferred embodiment the reconstructor implements an iterative reconstruction algorithm. Iterative reconstruction is based on a forward model function or simply referred to as the forward model. In a linear setting the forward model reduces to the familiar system matrix that implements the geometrical forward projection, essentially a summation of voxel values along line integrals that are then mapped onto the respective pixel position in projection space. But the reconstruction algorithm as proposed herein is not restricted to linear forward problems but can also be used with benefit for non-linear forward problems.

As briefly hinted at earlier, the forward model explains the elements in the projection space given a certain distribution of the quantity of interest in image space. The forward model is a main component for an iterative reconstruction algorithm. Conceptually, the forward model allows forming so called residues that measure the deviation between the actually measured projection data (that is, the sinograms) and "synthetic" projection data predicted by the forward model. An objective function can then be set up in terms of the residues. The reconstruction then aims at optimizing said objective function to find an "optimal" image that best explains or "fits" the sinograms under the chosen forward model. In one embodiment, the objective function may be expressed, depending on context, as either cost function or as a utility function. The optimization is then either 1) to find a minimizer for the cost function or 2) to find a maximizer for the utility function. In the following the optimization that underlies the iterative reconstruction will be explained, by example only, in terms of a cost function to be minimized. However, this is not to be construed as limiting the method as described herein because numerical consideration may require a reformulation of the optimization problem from a cost function into a utility function and hence the minimization problem becomes one of maximization.

One way to set up a forward model for the two image signals, that is, the phase image and the dark field image, may be expressed as follows:

$$m_\delta = \partial_r A \delta \quad m_\epsilon = A \epsilon \quad (1)$$

where A ("system matrix") is the geometrical forward projection operator (also used in conventional iterative CT reconstruction). Each entry in A represents the contribution of a voxel k to a measured line integral i as the line intersection length of the geometrical ray with the voxel (If other basis function than voxels are used, e.g., blobs, then the line integral along the ray through the basis function). The differential operator $\partial r$ indicates the partial derivative in radial direction (shown as z in FIG. 1). The beam geometry in (1) may be assumed parallel, but we will generalize this, on which more below.

Mathematically, the observed effect as discussed above per the exemplary imagery in FIGS. 2-4 is a cross-talk between the scatter and the phase image. It is proposed then herein to account for this cross-talk by including the cross-talk through a suitable model component into an iterative reconstruction procedure.

As evident from (1), for the following embodiment it will be assumed that the intensities as recorded at the detector have been split up or have been resolved into the two sinograms, the phase contrast sinogram $m_\delta$ and the dark field sinogram $m_\epsilon$, respectively, by operation of the previously mentioned signal Fourier analyzer or other suitable signal resolver or analyzer. To each of the channels there can then be formulated a forward projector A as per the left or right hand side in equation 1. Unlike previous approaches it is now proposed herein to merge or combine the dark field signal forward projector with the phase contrast signal forward projector as per the following equation (or mathematical equivalents thereof):

$$m_\delta = \partial_r A \delta \quad m_\epsilon = A \epsilon + \alpha |\partial_r^2 A \delta| \quad (2)$$

In particular, the phase contrast forward projector is merged or combined with the dark field forward projector to form a composite forward model (equation to the right in (2)) for the dark field image signal $m_\epsilon$ in order to acknowledge the signal contribution of edges in the phase image to the measured dark field projection data $m_\epsilon$. Put yet differently, it is proposed to mix the phase contrast and the dark-field signals. The forward model for the dark field signal includes is a composite forward model in the sense that it is formed by a linear or non-linear combination of the forward models of the phase and dark-field image. In the embodiment of eq (2), forming the composite includes addition and taking the partial radial derivate of the forward model of the phase signal. Other combinations may also be suitable and are envisaged herein. Taking the derivate gives rise to a model component $\alpha |\partial_r^2 A \delta|$ configured to capture the cross-talk from the phase signal. In other words the voxel in the relevant plane are forward projected into projection space as line integral and said line integrals are then differentiated twice along the current radial direction r (shown as z in FIG. 1). In the embodiment of eq (2), forming the composite includes taking the second partial derivate in radial direction, that is, in a direction perpendicular to the direction in which the trenches of the gratings are run. This corresponds to direction z in FIG. 1. Of course r will change with projection direction so in each row on the sinogram r will be in general different. The structure of the cross-talk model component may be understood a follows: the first partial derivate $\partial r$ corresponds to the modelling approach for phase change, that is, the change in propagation direction of the wave front. The second partial derivate then corresponds to the change of curvature of the wave front. In other words, the contribution of the phase contrast (the "edge" signals) into the dark field signal is modelled in "doubly differential" manner.

In the model (2), A denotes the system matrix or geometrical forward projection operator as introduced earlier above at (1). Although A itself is linear, the composite forward model (right equation in (2)) itself is non-linear because of the absolute value operator |•| which is non-linear. Again, A may be configured for parallel beams or may be configured for divergent beams (e.g., fan or cone) on which more later below.

The proposed iterative reconstruction can then be obtained in one embodiment by driving the reconstruction in particular by minimizing the cost function (or mathematical equivalents thereof):

$$\Delta = |W_\delta(m_\delta - \partial_r A\delta)|^2 + |W_\epsilon(m_\epsilon - A\epsilon - \alpha|\partial_z^2 A\delta|)|^2 + R(\delta, \epsilon) \quad (3)$$

where $W_\delta$ and $W_\epsilon$ are weighting parameters, for instance but not necessarily, statistical weighting matrices (assuming a statistical model for the measurement) and in one embodiment there is a regularizer or penalizer term R for the images $\delta$ and $\epsilon$. The parameter $\alpha$ denotes an empirical (or analytically derived) scaling factor.

Optimization of (3) as function of voxel images $\delta$ and $\epsilon$ can be performed for instance using a standard non-linear conjugate gradient algorithm or any other suitable optimization method, e.g., augmented Lagrangian methods or iterative coordinate descent etc.

The cost function is expressed in terms of the residues for the two signal channels, phase and dark-field, wherein the residue for the dark-field signal is formed using the new composite forward model with the cross-talk component. The residues from the two channels are square-sum combined into a single objective function or cost function A so the two images $\epsilon$, $\delta$ are reconstructed together in each iteration step.

In one embodiment, application of a suitable numerical technique (such as the conjugate gradient algorithm) for minimizing the cost function A then leads to an iterative expression that defines an update function for the iterative reconstruction. Using an initial guess for the dark-field image (which may be as simple as setting each voxel to zero), one then keeps updating using the update function through the iterations. In one embodiment one then repeatedly evaluates the cost function, not necessarily for each iteration, to check whether the cost $\Delta$ has dropped below a threshold. If it has, the iteration aborts and the latest image is the then output as the dark-field image. In other embodiments there is a fixed, pre-defined threshold number of iterations, and the iterative reconstruction terminates once this threshold has been reached. In some context, the phase contrast image is also of interest which may be output as well because the two have been reconstructed together.

The new iterative reconstruction algorithm may then be summarized by way of flow chart FIG. 5 as follows.

In general, at step S505 interferometric projection data is received. The interferometric projection data was detected at the detector at different viewing angles and recorded after signal processing as two sinograms $m_\epsilon$ and $m_\delta$ for the two signal channels, phase contrast $m_\delta$ and dark-field $m_\epsilon$.

At step S510 an iterative reconstruction algorithm is then carried out based on the measured sinograms and the objective function as per eq (3) or mathematical equivalents thereof.

After a sufficient number of iterations (as established by pre-defined abort criteria such as evaluating the cost function), the reconstructed cross sectional dark field at the considered scan position is output at step S515. In addition, the phase contrast image may also be output or stored for further reference.

It will be understood that the above defined steps yield a cross sectional image for one scanned position and the above mentioned step will need to be repeated for different scan positions to obtain the whole volume.

As per eq (4), the weights w may not necessarily have a statistical meaning as envisaged herein but may simply be chosen from a modeling perspective as weights that define the relative preponderance of the respective channels for the total cost $\Delta$.

But when a statistical approach is used, sometimes referred to as statistical iterative reconstruction, the weights may be chosen to represent the measurement uncertainty, that is, the variances and or standard deviations at the respective detector pixels px. The form of the statistical weights w is a function of the chosen statistical model for the measurements. In particular, the Poisson distribution may be assumed. The objective function can then be understood in this statistical setting as a (negative) maximum likelihood function. This is the maximum likelihood (ML) approach as for instance described in T. Koehler et al, "Iterative reconstruction for differential phase contrast imaging", pp 4542-4545, Med. Phys. 38 (8), August 2011. See for instance p 4543, left column, eq (3). This text is incorporated herein by reference in its entirety.

In a preferred embodiment, whether or not statistical, expansion of voxel values in terms of basis functions is used. In this basis function approach, each voxel is thought of as a linear combination of basis functions (sometimes also referred to as "blobs" related to the family of 2D-Kaiser-Bessel functions). Details of this approach can be found in T. Koehler et al, "Iterative reconstruction for differential phase contrast imaging", pp 4542-4545, Med. Phys. 38 (8), August 2011. In other words each value at a certain voxel can be thought of as a linear combination of weights formed from the basis functions and corresponding scalars. The iterative reconstruction then becomes an exercise of finding the optimal scalar components of the respective linear combination. This has the advantage that no finite difference approximations of the derivatives or as per eqs (2), (3) need to be used. Approximation by finite differences can be avoided in the basis function approach as the projections of the derivatives of the basis functions can be computed exactly as the basis functions are chosen to be analytically differentiable. In other words taking the derivative amounts to forming pre-defined analytical expression rather than using approximations through finite differences.

Turning now to a different embodiment, the common forward model is set up as per the following (or mathematical equivalents thereof):

$$I_i = I_{0i} e^{-\int_{l_i} \mu(x)dx} \left[ 1 + V_{0i} e^{-\int_{l_i} \epsilon(x)dx - \alpha \left|\partial_z^2 \int_{l_i} \delta(x)dx\right|} \cdot \cos\left(\varphi_{0i} + \partial_z \int_{l_i} \delta(x)dx\right) \right] \quad (4)$$

with:
$I_i$: Model for measured intensity through object along line $l_i$ at phase step i
$I_{0i}$: Measured intensity without object along line $l_i$
$V_{0i}$: Visibility along line $l_i$
$\varphi_{0i}$: Initial phase along line $l_i$
$\mu(x)$: absorption of object
$\epsilon(x)$: small angle scattering of object
$\delta(x)$: refractive index of object
z: direction perpendicular to the gratings,
x: position along line $l_i$.

In this forward model, no split up of the recorded intensities into a dark field sinogram $m_\epsilon$ and phase contrast sinogram $m_\delta$ is necessary. In other words according to this embodiment the input is formed by the common sinogram m where each entry is composed of the respective time series recorded at the detector in the phase stepping.

The signal model as per eq (4) forms a common forward model for the common sinogram as compared with the previous embodiment, where, as per eqs (2), there is a dedicated forward model for the two channels (phase and dark-field) corresponding to the left and right equations in (2). The common forward model still includes model components for the two signals, namely model component $\partial_z \int_{l_i} \delta(x) dx$ for the phase signal and model component $$e^{-\int_{l_i} \varepsilon(x) dx}$$

for the dark-field. A forward model, only visually similar to eq (4) above, has been reported by A Ritter et al in "Simultaneous maximum-likelihood reconstruction for x-ray grating based phase-contrast tomography avoiding intermediate phase retrieval". See page 2, Eq (3) in Ritter. Crucially however and very much unlike Ritter, the forward model includes, as in the previous embodiment eq (4), a model component that captures the cross-talk from phase signal into the dark-field signal as per:

$$\alpha |\partial_z^2 \int_{l_i} \delta(x) dx| \quad (5)$$

With the model component for the dark-field signal being combined with said cross-talk component (5) as per equation (4). Coming back to the system matrix approach as per the previous embodiment (2), it may be instructive to draw a structural analogy with the common model signal model (4). The rows (or depending on convention, the columns) of A correspond to numerical discretizations of the (intermediate) phase signal model component $\int_{l_i} \delta(x) dx$.

The cost function for this non-linear forward model can then be formulated similar to eq (4) above as per the following (or mathematical equivalents thereof):

$$\Delta(\mu, \varepsilon, \delta) = \sum_i w_i (I_i(\mu, \varepsilon, \delta) - m_i)^2 + \beta R(\mu, \varepsilon, \delta) \quad (6)$$

where the $w_i$ are weighting factors estimated for the intensity measurements (for instance derived from the assumption that the measurement signals follow a Poisson distribution) and where the $m_i$ are the measured intensities (or photon counts, depending on detector type) per phase step i.

In other words, in this embodiment at step S505 the common sinogram comprising the respective intensities series for the respective projection directions is received instead of the two dedicated sinograms.

The remaining steps S510 and S515 are similar to the embodiment explained earlier: The cost function is again formulated in terms of a residue, but this time in respect for the common forward model and the intensities $m_i$ as recoded without pre-processing by signal analyzer SA. As in eq (3) of the previous embodiment with the dedicated forward models as per eq (2), eq (6) defines an optimization problem, in particular one for finding minimizers ($\mu$, $\varepsilon$, $\delta$). Solution of the optimization problem then yields in particular the dark field image $\varepsilon$.

A suitable iterative numerical optimization algorithm for cost function (6) (such as the conjugated gradients method or others as mentioned above) may be used to arrive at an update function. This update function then defines the iterative reconstruction algorithm for in particular the dark-field image $\varepsilon$ problem (but also for the other two images $\mu$, $\delta$ as these are in general solved for together with the dark-field image $\varepsilon$).

Just as in the previous embodiment (3), one may chose a statistical approach such as ML. In particular, the $w_i$'s can then be chosen as statistical weights assuming an underlying statistical distribution, for instance Poisson or Gaussian for the measured data.

The cost function at eq (6) is formulated for a certain scan position and pixel position where the index i extends over the different intensities measures for said pixel across the different phase steps i. Corresponding optimization problems will need to be solved for all scan positions of interest to cover the whole volume of interest.

In either of the two embodiments for the forward models (2), (4), a regularization or penalizer term R may be used to enforce certain desirable behavior such as smoothness of the solutions. For instance in one embodiment a Tikhonov regularizer is used but other regularizers R are also envisaged herein. In embodiment there is a factor $\beta$ to adjust the response of the regularizer term.

In the second embodiment as described earlier for the first embodiment, again a basis function can be used to improve the accuracy of the proposed method so as to express the derivatives analytically rather than having to approximate the same by finite differences.

It will be appreciated that in both embodiments, the forward projection operator is non-linear. However, other embodiments may also be envisaged where the forward projector is linear.

Coming now back to beam geometry, in some of the above embodiments it has been assumed that the beam geometry is parallel. For a divergent geometry, such as cone or fan beam, a correction is applied for instance as described in Applicant's WO 2013/171657. The correction is applied to the forward model. In the embodiment (2) with the respective dedicated forward models for the phase and dark-field signal, it is envisaged in a preferred embodiment to apply the divergent beam geometry correction only to the forward model dedicated to the dark field signal (that is, to the right equation in (2))—of course this additional modeling involves the special dependence of the dark field signal on the magnification of the system. See for instance the correction term d=$\alpha$/M as per equation (7) in the above cited reference WO 2013/171657. Of course, the mere geometrical change in geometry when moving from parallel beams to divergent beams still needs to be taken into account in the forward model formulation for both signals so that the rows of the system matrix A still provide the numerical implementation of the corresponding line integrals. In other embodiments, the correction may be applied to both of the dedicated models.

As to the common forward model (4) the following modification may be applied for divergent beam geometries:

$$I_i = I_{0i} e^{-\int_{l_i} \mu(x) dx} \left[ 1 + V_{0i} e^{-\int_{l_i} \frac{x}{L} \varepsilon(x) dx - \alpha |\partial_z^2 \int_{l_i} \delta(x) dx|} \cdot \cos\left( \varphi_{0i} + \partial_z \int_{l_i} \delta(x) dx \right) \right] \quad (7)$$

In the modelling approach as per (6) the only difference over the embodiment (5) (where a parallel beam geometry is assumed) is the inclusion of an additional weighting factor x/L in the modelling component for the dark field signal. This is due to scattering, with L (shown a d in FIG. 1) being the distance from the source to the phase grating. Note that this weighting "breaks" the symmetry of the usual line integrals, thus, the integration needs to be performed along the line $l_i$ from the source to the detector (or vice versa, from detector to source, in which case the weighting is taken as (L−x)/L) as opposed to traditional line integrals where the value of the line integral is independent of the direction of integration.

The reconstructor RECON may be run on a general purpose computer that serves as an operator console (not shown) for the imaging system or as a work station for image review. In another embodiment the reconstructor is arranged as a dedicated module, in particular a dedicated programmable chip, for instance an FGPA chip or may be implemented as a hard wired chip.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An image signal processing apparatus configured for improving fidelity or accuracy of dark field images in differential X-ray phase contrast imaging, the image signal processing apparatus comprising:
   a signal input port configured to receive from a detector interferometric measurement data detected by the detector in response to an X-ray beam incident on said detector after projection of said beam through a specimen to be imaged, the data comprising a phase contrast signal and a dark field signal;
   a processor configured to execute an image reconstruction algorithm to reconstruct at least the dark field signal into a dark field image, wherein the reconstructing of at least the dark field signal into the dark field image is based on a forward model that incorporates a model component configured to capture cross-talk of the phase contrast signal into the dark field signal; and
   an image output port configured to output to a display device at least the reconstructed dark field image.

2. The apparatus of claim 1, wherein the forward model is a composite forward model formed from a combination of i) a dedicated forward model for a differential phase contrast signal and ii) a dedicated forward model for the dark field signal.

3. The apparatus of claim 1, wherein a cross-talk model component is proportional to an absolute value of a partial spatial derivative of a dedicated forward model for the differential phase contrast signal.

4. The apparatus of claim 1, wherein the forward model is a common one for both, the phase contrast signal and the dark field signal.

5. The apparatus of claim 4, wherein the common forward model includes a model component for the phase contrast signal and a model component for the dark field signal, wherein a cross-talk model component is proportional to an absolute value of a partial spatial derivative of the model component for the phase contrast signal.

6. The apparatus of claim 1, wherein the reconstruction algorithm is iterative.

7. The apparatus of claim 6, wherein iterations of the iterative reconstruction algorithm are driven by an optimization of an objective function.

8. The apparatus of claim 7, wherein the objective function incorporates a residue in respective of the forward model.

9. The apparatus of claim 1, wherein a geometry of the beam is parallel or divergent.

10. An interferometric X-ray imaging system configured for improving fidelity or accuracy of dark field images in differential X-ray phase contrast imaging, the interferometric X-ray imaging system comprising:
an apparatus that comprises
 a signal input port configured to receive from a detector interferometric measurement data detected by the detector in response to an X-ray beam incident on said detector after projection of said beam through a specimen to be imaged, the data comprising a phase contrast signal and a dark field signal;
 a processor configured to execute an image reconstruction algorithm to reconstruct at least the dark field signal into a dark field image, wherein the reconstructing of at least the dark field signal into the dark field image is based on a forward model that incorporates a model component configured to capture cross-talk of the phase contrast signal into the dark field signal; and
 an image output port configured to output to a display device at least the reconstructed dark field image.

11. An image signal processing method for improving fidelity or accuracy of dark field images in differential X-ray phase contrast imaging, the image signal processing method comprising:
receiving interferometric measurement data detected at a detector in response to an X-ray beam incident on said detector after projection of said beam through a specimen to be imaged, the data comprising a phase contrast signal and a dark field signal;
reconstructing at least the dark field signal into a dark field image, with a reconstruction algorithm, wherein the reconstructing of at least the dark field signal into the dark field image is based on a forward projection model that incorporates a model component configured to capture cross-talk of the phase contrast signal into the dark field signal; and
outputting at least the reconstructed dark field image.

12. A non-transitory computer program element for controlling an apparatus or system, which, when being executed by a processing unit is adapted to perform the method of claim 11.

13. The non-transitory computer program element of claim 12 stored as part of a computer readable medium.

* * * * *